US006479521B2

(12) United States Patent
Exner et al.

(10) Patent No.: US 6,479,521 B2
(45) **Date of Patent: *Nov. 12, 2002**

(54) USE OF 2-MERCAPTO-PYRIDINE-N-OXIDE

(75) Inventors: Otto Exner, Ratingen (DE); Heinz-Joachim Rother, Krefeld (DE); Martin Kugler, Leichlingen (DE); Hartmut Rehbein, Moers (DE)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/445,330

(22) PCT Filed: Jun. 2, 1998

(86) PCT No.: PCT/EP98/03260

§ 371 (c)(1),
(2), (4) Date: Dec. 6, 1999

(87) PCT Pub. No.: WO98/56959

PCT Pub. Date: Dec. 17, 1998

(65) Prior Publication Data

US 2002/0147227 A1 Oct. 10, 2002

(30) Foreign Application Priority Data

Jun. 13, 1997 (DE) ........................................ 197 25 017

(51) Int. Cl.[7] ................................................ A61K 31/44
(52) U.S. Cl. ........................................................ 514/345
(58) Field of Search ......................................... 514/345

(56) References Cited

U.S. PATENT DOCUMENTS

| | | | | |
|---|---|---|---|---|
| 2,809,971 A | * 10/1957 | Bernstein et al. | ........... | 260/270 |
| 4,474,760 A | * 10/1984 | Hill | ............................ | 424/174 |
| 4,830,657 A | * 5/1989 | Jakubowski et al. | ........... | 71/67 |
| 5,451,577 A | * 9/1995 | Morpeth | ..................... | 514/186 |
| 5,464,622 A | * 11/1995 | Mehta et al. | ............... | 514/345 |

FOREIGN PATENT DOCUMENTS

| | | | |
|---|---|---|---|
| EP | 0366071 | * 10/1989 | ................. 514/186 |

OTHER PUBLICATIONS

Microbicides for the Protection of Materials, Winfried Paulus, (month unavailable) 1993, Chapman & Hall, pp. 294–300, Pyridine–N–oxides.

* cited by examiner

*Primary Examiner*—James H. Reamer
(74) *Attorney, Agent, or Firm*—Joseph C. Gil; Richard E. L. Henderson; Diderico van Eyl

(57) ABSTRACT

The present application relates to the use of 2-mercapto-pyridine N-oxide and/or its alkali metal and alkaline earth metal salts and its metal complexes for the preservation of animal skins and leather.

6 Claims, No Drawings

USE OF 2-MERCAPTO-PYRIDINE-N-OXIDE

The present application relates to the use of 2-mercapto-pyridine N-oxide and/or a metal complex thereof for the preservation of animal skins and leather.

2-Mercapto-pyridine N-oxide and its use as a preservative for cosmetics are known (Microbicides for the Protecting of Materials, Baulens; 1993 Chepron & Hall, pages 294–300).

It has now surprisingly been found that 2-mercapto-pyridine N-oxide, its salt and metal complexes permit excellent and permanent protection of the animal skins and leather from microbial attack during production and storage thereof.

The application therefore relates to the use of 2-mercapto-pyridine N-oxide and/or its salts and/or metal complexes for the preservation of animal skins and leather.

2-Mercapto-pyridine N-oxide is preferably used in combination with at least one further active ingredient suitable for the protection of animal skins and leather. In particular, mercaptobenzothiazole, methylene bisthiocyanate, thiocyanatomethylthiobenzothiazole (TCMTB), octylisothiazolinone, N-cyclohexylbenzothiophene-2-carboxamide s,s-dioxide and preferably phenolic compounds are suitable as further active ingredients for combination with 2-mercapto-pyridine N-oxide.

These combinations have outstanding and synergistic properties and are likewise the subject of the application.

Suitable phenolic active ingredients are preferably phenol derivatives, such as tribromophenol, trichlorophenol, tetrachlorophenol, nitrophenol, 3-methyl-4-chlorophenol, 3,5-dimethyl-4-chlorophenol, phenoxyethanol, dichlorophene, o-phenylphenol, m-phenylphenol, p-phenylphenol, 2-benzyl-4-chlorophenol, 2,4-dichloro-3,5-dimethylphenol, 4-chlorothymol, chlorophene, triclosan, fentichlor and ammonium, alkali metal and alkaline earth metal salts thereof and mixtures thereof.

Preferred 2-mercapto-pyridine N-oxide salts and metal complexes are the sodium and potassium salts and copper and zinc complexes.

Combinations of 3,5-dimethyl -4-chlorophenol, 2-benzyl4-chlorophenol, 3-methyl-4-chlorophenol p-chloro m-cresol (CMC)) and/or o-phenylphenol (OPP) as phenolic components and 2-mercapto-pyridine N-oxide and/or its alkali metal and alkaline earth metal salts and its metal complexes are preferred.

Particularly preferred combinations are the combinations of OPP and/or CMC with 2-mercapto-pyridine N-oxide and/or with its abovementioned salts and complexes.

In particular, mixtures containing CMC and 2-mercapto-pyridine N-oxide Na salt and optionally OPP and their use according to the invention are preferred.

The mixing ratios of 2-mercapto-pyridine N-oxide are in general 1 part by weight to 5 to 200, preferably 10 to 100, in particular 12 to 50, parts by weight of the further active ingredients or active ingredient mixtures.

The ratio of the further active ingredients, in particular of the phenolic compounds, with one another may be widely varied and can be readily determined by customary experiments. In the case of a mixture of, for example, OPP and CMC, the ratio is preferably 1:1 to 1:5.

The abovementioned active ingredient and the mixtures of the active ingredients are generally used in the form of formulations. The concentration for use is preferably 0.1 to 1% of active ingredient or active ingredient mixture, relative to the skins or leather to be protected.

The compositions formed during formulation preferably contain 10 to 50% of the active ingredient or of the active ingredient mixture. In general, the compositions contain, as further components, 10 to 30% of alkali metal hydroxides and/or alkaline earth metal hydroxides; 1 to 20% of ionic and/or nonionic emulsifiers; 5 to 30% of organic solvents, such as, in particular, glycols, ketones, glycol ethers and alcohols, such as ethanol, methanol, 1,2-propanediol, n-propanol or 2-propanol, and 0–0.5% of aromas and fragrances. The remainder to 100% is water.

According to the invention, the active ingredient and the active ingredient mixtures and the compositions which can be prepared therefrom are used according to generally customary methods of use in leather production, for protecting animal skins from attack and damage by microorganisms. Of particular interest is the fact that members of the species *Aspergillus niger, Aspergillus repens, Hormoconis resinae, Penicillium glaucum* and *Trichloderma viride*, Penicillium species, such as *P. citrinum* or *P. glaucum, Paecilomyces variotii*, Cladosporium species, such as Mucor species, such as *Mucor mucedo*, Rhizopus species, such as *Rhizopus oryzae, Rhizopus rouxii*, are completely and permanently suppressed.

The following Examples serve for illustrating the invention and are not limited to this.

EXAMPLE 1

Agar plates are contaminated with conidia of the species *Aspergillus niger, Aspergillus repens, Penicillium glaucum, Trichoderma viride* and *Hormoconis resinae*. Wet chrome leathers treated with mixture I, II and mixture III (wet blue) are then placed on top and incubated for 28 days at 95% relative humidity and 20 to 30° C.

| |
|---|
| Mixture I |
| 30 parts by weight of p-chloro-m-cresol |
| 13 parts by weight of o-phenylphenol |
| Mixture II |
| 30 parts by weight of p-chloro-m-cresol |
| 13 parts by weight of o-phenylphenol |
| 1.2 parts by weight of 2-mercapto pyridine N-oxide Na salt |
| Mixture III |
| 37 parts by weight of p-chloro-m-cresol |
| 1.2 parts by weight of 2-mercapto-pyridine N-oxide Na salt |

The wet blues preserved with the mixture I exhibit growth of mould on the test specimens after an incubation time of only 10 days. In the case of mixture II and III, no attack is found after an incubation time of 28 days.

EXAMPLE 2

Formulation I 27 parts by weight of p-chloro-m-cresol
12 parts by weight of o-phenylphenol
1.2 parts by weight of 2-mercapto-pyridine N-oxide Na salt
12 parts by weight of NaOH
14.2 parts by weight of 1,2-propanediol
Remainder to 100 parts by weight water

Formulation II 37 parts by weight of p-chloro-m-cresol
1.2 parts by weight of 2-mercapto-pyridine N-oxide Na salt
10.5 parts by weight of NaOH 14 parts by weight of 1,2-propanediol
Remainder to 100 parts by weight water Formulation III 30 parts by weight of p-chloro-m-cresol
1.2 parts by weight of 2-mercapto-pyridine N-oxide Na salt
8.5 parts by weight of NaOH
14 parts by weight of 1,2-propanediol
Remainder to 100 parts by weight water

What is claimed is:

1. A composition comprising (a) 2-mercaptopyridine N-oxide and (b) a compound selected from the group consisting of (i) mercaptobenzothiazole, (ii) methylene bisthiocyanate, (iii) thiocyanatomethylthiobenzothiazole, (iv) N-cyclohexylbenzothiophene-2-carboxamide s,s-dioxide, (v) a phenolic compound, and (vi) mixtures thereof.

2. A composition according to claim 1 wherein the phenolic compound is selected from the group consisting of tribromophenol, trichlorophenol, tetrachlorophenol, nitrophenol, 3-methyl-4-chlorophenol, 3,5-dimethyl-4-chlorophenol, phenoxyethanol, dichlorophene, o-phenylphenol, m-phenylphenol, p-phenylphenol, 2-benzyl-4-chlorophenol, 2,4-dichloro-3,5-dimethylphenol, 4-chlorothymol, chlorophene, triclosan, fentichlor, ammonium, alkali metal, alkaline earth metal salts thereof, mixtures of such phenolic compounds and salts thereof.

3. A composition according to claim 1 wherein the phenolic compound is o-phenylphenol and/or 3-methyl-4-chlorophenol.

4. A composition according to claim 1 additionally comprising alkali metal hydroxides and/or alkaline earth metal hydroxides, ionic and/or nonionic emulsifiers, solvents, and optional aromas or fragrances.

5. A method for protecting animal skins or leather from microbial attack comprising applying, to an animal skin or leather, a composition comprising (a) 2-mercaptopyridine N-oxide and (b) a compound selected from the group consisting of (i) mercaptobenzothiazole, (ii) methylene bisthiocyanate, (iii) thiocyanatomethylthiobenzothiazole, (iv) N-cyclohexylbenzothiophene-2-carboxamide s,s-dioxide, (v) phenolic compounds, and (vi) mixtures thereof.

6. An animal skin, leather, or leather production product protected with a a composition comprising (a) 2-mercaptopyridine N-oxide and (b) a compound selected from the group consisting of (i) mercaptobenzothiazole, (ii) methylene bisthiocyanate, (iii) thiocyanatomethylthiobenzothiazole, (iv) N-cyclohexylbenzothiophene-2-carboxamide s,s-dioxide, (v) phenolic compounds, and (vi) mixtures thereof.

* * * * *